United States Patent [19]

Nickisch et al.

[11] Patent Number: 4,789,668
[45] Date of Patent: Dec. 6, 1988

[54] 1α,7α-DITHIO-SUBSTITUTED SPIROLACTONES, PROCESSES FOR THEIR PREPARATION, AND THEIR USE AS MEDICINES

[75] Inventors: Klaus Nickisch; Henry Laurent; Dieter Bittler; Rudolf Wiechert; Wolfgang Losert, all of Berlin, Fed. Rep. of Germany

[73] Assignee: Schering Aktiengesellschaft, Berlin and Bergkamen, Fed. Rep. of Germany

[21] Appl. No.: 929,292
[22] PCT Filed: Feb. 13, 1986
[86] PCT No.: PCT/DE86/00055
  § 371 Date: Oct. 17, 1986
  § 102(e) Date: Oct. 17, 1986
[87] PCT Pub. No.: WO86/04900
  PCT Pub. Date: Aug. 28, 1986

[30] Foreign Application Priority Data
  Feb. 18, 1985 [DE] Fed. Rep. of Germany ....... 3506100

[51] Int. Cl.⁴ .................. A61K 31/585; C07J 53/00
[52] U.S. Cl. ........................................ 514/173; 540/15
[58] Field of Search ........................... 540/15; 514/173

[56] References Cited
U.S. PATENT DOCUMENTS
3,013,012 12/1961 Cella et al. ........................... 540/42

FOREIGN PATENT DOCUMENTS
99853 1/1984 European Pat. Off. .

OTHER PUBLICATIONS
Karim et al., "Isolation and Identification of Novel Sulfur-Containing Metabolites of Spironolactone" Stercias, 20:1, pp. 41–62, (1972).

Primary Examiner—Leonard Schenkman
Assistant Examiner—Joseph A. Lipovsky
Attorney, Agent, or Firm—Millen & White

[57] ABSTRACT

The disclosure relates to novel 1α,7α-dithio-substituted spirolactones of general Formula I

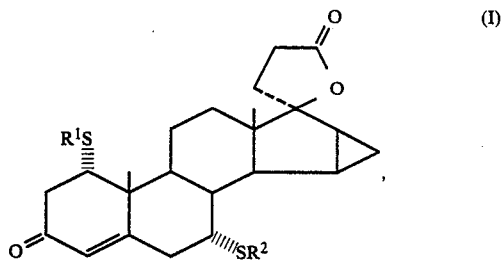

wherein
$R^1$ is $C_{1-3}$-alkyl and $C_{1-3}$-acyl and
$R^2$ is hydrogen, $C_{1-3}$-alkyl and $C_{1-3}$-acyl, to their preparation, and to their use as medicinal agents.

The compounds of this invention exhibit anti-aldosterone activity and show the profile of effectiveness of a pro-drug.

14 Claims, No Drawings

1α,7α-DITHIO-SUBSTITUTED SPIROLACTONES, PROCESSES FOR THEIR PREPARATION, AND THEIR USE AS MEDICINES

The invention relates to novel 1α,7α-disubstituted spirolactones, processes for their production, and pharmaceutical preparations containing same, in accordance with the patent claims.

$R^1$ in Formula I, when meaning an alkyl residue of 1–3 carbon atoms, represents, for example, a methyl, ethyl, propyl or isopropyl group.

$R^1$ in Formula I, when meaning an acyl residue of 1–3 carbon atoms, represents, for example, the formyl, acetyl and propionyl group.

The novel compounds of general Formula I have the property of neutralizing or reversing the effect of aldosterone or desoxycorticosterone on the excretion of sodium and potassium. Consequently, the compounds of this invention are suitable for the treatment of certain forms of hypertension, of edemas, e.g. in cardiac insufficiency, of cirrhosis of the liver and nephrotic syndrome, of primary and secondary aldosteronism and other endocrinological disorders caused by aldosterone. They can furthermore be utilized as diuretics.

The active compounds of this invention, as compared with the commercially available spironolactone and its metabolites which contain a mercapto or methylthio group in the 7α-position in place of the acetylthio group (Steroids 20 : 41 [1972]), exhibit the advantage of higher activity and prolonged duration of effectiveness, the onset of activity also being retarded. This profile of activity indicates that the compounds of this invention involve biologically active compounds which are metabolically activated only within the organism, namely so-called pro-drugs.

Such compounds exhibit the advantage when used medicinally that the content of active agent in the blood plasma is exposed to less extensive fluctuations.

The compounds of this invention are furthermore distinguished by being inactive endocrinologically. For example, they show practically no binding to the androgen receptor.

The compounds according to this invention which contain a thio group in the 1α as well as 7α-position prove to be superior in their antialdosterone activity over the known spironolactone in a test model of Hollmann (Naunyn-Schmiedebergs Arch. Exp. Path. Pharmak. 247 : 419 [1964]) and are distinguished over spironolactone by delayed onset of effectiveness.

1α,7α-Diacetylthio-15β,16β-methylene-3-oxo-17α-pregn-4-ene-21,17-carbolactone proved to be especially valuable pharmacologically.

The novel active agents actually can be used in the same way as spironolactone. The dosage of the active agents lies below that for spironolactone. However, on account of the longer-lasting effect, the novel active compounds normally need to be administered only once daily.

The active compounds can be processed according to conventional methods of galenic pharmacy into pharmaceutical preparations, preferably for enteral administration. Particularly suitable for enteral administration are tablets, dragees or capsules containing per dosage unit about 25–200 mg of active ingredient in an inert excipient.

The compounds of this invention corresponding to general Formula I are produced by conventional methods.

Compounds of formula I can be made by reacting a 1,2-unsaturated spirolactone of Formula II, which has the general formula

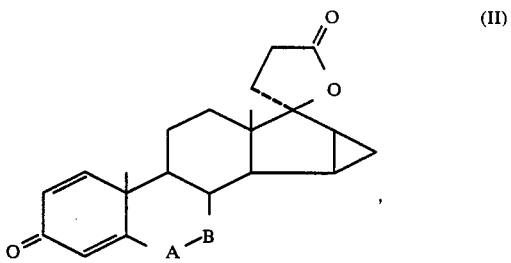

wherein —A—B— is —CH=CH—,

—CH$_2$—CH—SCH$_3$, or —CH$_2$—CH—SH in a conventional manner, (a) with a thioalkanoic acid in a proton solvent, or (b) with an alkanethiol in a protonic solvent in the presence of a base and optically esterifiying a free mercapto group with an active acid derivative.

For preparing the compounds of this invention which contain an acylthio group in the 1α- and 7α-positions, the Δ$^{1,4,6}$-unsaturated 3-ketopregnatriene of Formula II is suitably dissolved in a protonic solvent suited for this purpose, or in a mixture thereof, the desired thioalkanoic acid is added thereto, and the reaction mixture is heated to temperatures above room temperature up to the boiling temperature of the solvent. Suitable solvents and, respectively, mixtures thereof are methanol, acetone and tetrahydrofuran. Optionally employed solubilizers, such as diisopropyl ether, benzene and heptane, do not interfere with the course of the reaction.

In order to produce compounds of Formula I having an alkylthio group in the 1α-position and in the 7α-position, the starting material of Formula II is reacted in a suitable solvent with the corresponding alkyl mercaptan. Suitable solvents are, in particular, organic bases, such as pyridine, piperidine, collidine and lutidine. The reaction mixture can be heated to temperatures above room temperature in case extremely long reaction periods are undesirable.

For preparing compounds of Formula I exhibiting nonidentical substituents $R^1$ and $R^2$ in the 1α-position and the 7α-position, the procedure is such that either the 1α,7α-disubstituted compounds of Formula I are used as the starting materials and these are partially cleaved to the corresponding Δ$^1$-unsaturated compounds of Formula II; or that a compound of Formula II is initially used as the starting compound which is unsaturated in the 1,2-position and is substituted in the 7α-position by a mercapto, acetylthio or methylthio group.

The partial splitting off of an alkylthio group takes place with an alkali metal alcoholate, such as, for example, potassium methylate, at temperatures below room temperature.

The optionally following esterification of the mercapto group is conducted according to the processes customary in steroid chemistry for esterifications of sterols. Esterification takes place preferably with an activated derivative of a lower aliphatic carboxylic acid in the presence of pyridine and/or 4-dimethylaminopyridine. Especially suitable derivatives are the anhydrides and halogenides of lower carboxylic acids, particularly acetic and propionic acid.

The reaction products of this invention are separated by conventional methods, such as precipitation, filtration or extraction, and purified, for example, by chromatography and/or recrystallization.

Insofar as the starting compounds needed for performing the process of this invention are unknown, their preparation is described herein.

Preparation of Starting Material

A.

15β,16β-Methylene-7α-methylthio-3-oxo-17α-pregna-1,4-diene-21 17-carbolactone 4.0 g of 15β,16β-methylene-3-oxo-17α-pregna-4,6-diene-21,17-carbolactone is dissolved in 40 ml of methanol and 4 ml of piperidine. Under ice cooling, methanethiol is introduced from a steel bottle into the solution over a time period of 30 minutes. Subsequently, the mixture is allowed to stand for 15 hours at room temperature, and then the mixture is poured into ice water. The thus-precipitated product is filtered off, washed with water, dried, and chromatographed on silica gel. With 8.8–10.3% acetone-dichloromethane, 2.99 g is eluted and recrystallized from hexane-dichloromethane-diisopropyl ether. Yield: 1.80 g of 15β, 16β-methylene-7α-methylthio-3-oxo-17α-pregn-4-ene-21,17-carbolactone, mp 269° C.

UV: $\epsilon_{236}=16,000$ (in methanol).

A solution of 600 mg of 15β,16β-methylene-7α-methylthio-3-oxo-17α-pregn-4-ene-21,17-carbolactone in 12 ml of dioxane is combined with 660 mg of 2,3-dichloro-5,6-dicyano-1,4-benzoquinone and stirred for 17 hours at 100° C. The reaction mixture is diluted with diethyl ether, washed with sodium bicarbonate solution and water, dried, and evaporated. The residue is chromatographed on silica gel. After trituration with diisopropyl ether, 145 mg of 15β,16β-methylene-7α-methylthio-3-oxo-17α-pregna-1,4-diene-21,17-carbolactone is obtained, mp 265.3° C.

UV: $\epsilon_{244}=15,400$ (in methanol).

B.

7α-Mercapto-15β,16β-methylene-3-oxo-17α-pregna-1,4-diene-21,17-carbolactone 277 mg of potassium ethylate in 7 ml of methanol is added dropwise to a suspension, cooled to 0° C., of 640 mg of 7α-acetylthio-15β,16β-methylene-3-oxo-17α-pregna-1,4-diene-21,17-carbolactone (EPO 099 853) in 5 ml of methanol and 8 ml of tetrahydrofuran, and the mixture is stirred for one hour. The mixture is worked up by diluting with dichloromethane, washing with dilute sulfuric acid and water, drying over magnesium sulfate, and concentration under vacuum. The resultant crude product is purified by column chromatography, thus obtaining 296 mg of 7α-mercapto-15β,16β-methylene-3-oxo-17α-pregna-1,4-diene-21,17-carbolactone, mp 258.7° C.

$[\alpha]_D= +17°$ (in chloroform).

The examples set forth below are to describe the invention in detail.

EXAMPLE 1

A solution of 1.5 g of 15β,16β-methylene-3-oxo-17α-pregna-1,4,6-triene-21,17-carbolactone in 30 ml of methanol and 6 ml of water is combined with 2.1 ml of thioacetic acid and allowed to stand for 16 hours at room temperature. The mixture is worked up by diluting with diethyl ether, washing with sodium bicarbonate solution and water, drying over sodium sulfate, and evaporation under vacuum. The residue is chromatographed on silica gel; elution yields 570 mg of 1α,7α-diacetylthio-15β,16β-methylene-3-oxo-17α-pregn-4-ene-21,17-carbolactone.

UV: $\epsilon_{234}=16,400$ (in methanol).

$[\alpha]_D= -28°$ (in chloroform).

EXAMPLE 2

Methanethiol is introduced almost up to the saturation point into a solution of 8.6 g of 15β,16β-methylene-3-oxo-17α-pregna-1,4,6-triene-21,17-carbolactone in 86 ml of methanol and 1.72 ml of piperidine. The reaction mixture is then allowed to stand at room temperature for 16 hours. For working-up purposes, the mixture is diluted with methylene chloride, washed with water, dried over sodium sulfate, and evaporated under vacuum. The residue is chromatographed on silica gel. Trituration with diisopropyl ether yields 6.9 g of 15β,16β-methylene-1α,7α-dimethylthio-3-oxo-17α-pregn-4-ene-21,17-carbolactone, mp 129.1° C.

UV: $\epsilon_{240}=12,000$ (in methanol).

$[\alpha]_D= +12°$ (in chloroform).

EXAMPLE 3

(a) An ice-cooled solution of 6.0 g of 15β,16β-methylene-1α,7α-dimethylthio-3-oxo-17α-pregn-4-ene-21,17-carbolactone in 187 ml of ethanol is combined with 2.27 g of potassium ethylate and stirred for 45 minutes under cooling and while passing argon over the mixture. The latter is poured into ice water for working-up purposes. The thus-obtained precipitate is suctioned off, washed with water, and dried. Chromatography on silica gel and crystallization from acetone yield 3.1 g of 15β,16β-methylene-7α-methylthio-3-oxo-17α-pregna-1,4-diene-21,17-carbolactone, mp 267.4° C.

(b) Under the conditions described in Example 1, 1.0 g of 15β,16β-methylene-7α-methylthio-3-oxo-17α-pregna-1,4-diene-21,17-carbolactone is reacted and worked up. After chromatography on silica gel and trituration with diisopropyl ether, 960 mg of 1α-acetylthio-15β,16β-methylene-7α-methylthio-3-oxo-17α-pregn-4-ene-21,17-carbolactone is obtained, mp 192.3° C.

UV: $\epsilon_{239}=15,950$ (in methanol).

$[\alpha]_D= +15°$ (in chloroform).

EXAMPLE 4

Under the conditions disclosed in Example 1, 50 mg of 7α-mercapto-15β,16β-methylene-3-oxo-17α-pregna-1,4-diene-21,17-carbolactone is reacted and worked up. After layer chromatography, 45 mg of 1α-acetylthio-7α-mercapto-15β,16β-methylene-3-oxo-17α-pregna-4-ene-21,17-carbolactone is obtained.

UV: $\epsilon_{236}=11,600$ (in methanol).

$[\alpha]_D= +36.5°$ (in chloroform).

EXAMPLE 5

Methanethiol is introduced almost to saturation into a solution, cooled to −20° C., of 720 mg of 7α-mercapto-15β,16β-methylene-3-oxo-17α-pregna-1,4-diene-21,17-carbolactone in 28 ml of tetrahydrofuran. Then the reaction mixture is combined with 192 mg of potassium tert-butylate and stirred at the above temperature for 30 minutes. The mixture is worked up by pouring into ice water and neutralizing with acetic acid. The resultant precipitate is suctioned off, washed with water, and dried. Trituration with diisopropyl ether yields 760 mg of 7α-mercapto-15β,16β-methylene-1α-methylthio-3-oxo-17α-pregn-4-ene-21,17-carbolactone, mp 252.3° C.

UV: $\epsilon_{237} = 11,100$ (in methanol).

$[\alpha]_D = +62°$ (in chloroform).

EXAMPLE 6

A solution of 500 mg of 7α-mercapto-15β,16β-methylene-1α-methylthio-3-oxo-17α-pregn-4-ene-21,17-carbolactone in 2 ml of pyridine is combined with 1 ml of acetic anhydride and allowed to stand at room temperature for 3 hours. After ice water precipitation, the filtered-off and dried precipitate is recrystallized from diisopropyl ether/acetone, thus obtaining 440 mg of 7α-acetylthio-15β,16β-methylene-1α-methylthio-3-oxo-17α-pregn-4-ene-21,17-carbolactone, mp 251.8° C.

UV: $\epsilon_{236} = 16,100$ (in methanol).

$[\alpha]_D = -19°$ (in chloroform).

We claim:

1. 1α,7α-Dithio-substituted spirolactone of general Formula I

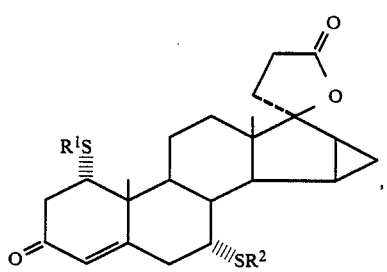

wherein
$R^1$ is $C_{1-3}$-alkyl or $C_{1-3}$-acyl and
$R^2$ is hydrogen or $C_{1-3}$-alkyl.

2. 1α-Acetylthio-15β,16β-methylene-7α-methylthio-3-oxo-17α-pregn-4-ene-21,17-carbolactone a compound of claim 1.

3. A pharmaceutical composition useful for treating hypertension comprising an effective amount of a compound of claim 2 and a pharmaceutically acceptable carrier.

4. A method for treating hypertension in a patient in need of such treatment comprising administering to said patient an effective amount of a compound of claim 2.

5. 15β,16β-Methylene-1α,7α-dimethylthio-3-oxo-17α-pregn-4-ene-21,17-carbolactone a compound of claim 1.

6. A pharmaceutical composition useful for treating hypertension comprising an effective amount of a compound of claim 5 and a pharmaceutically acceptable carrier.

7. A method for treating hypertension in a patient in need of such treatment comprising administering to said patient an effective amount of a compound of claim 5.

8. A pharmaceutical composition useful for treating hypertension comprising an effective amount of a compound of claim 1 and a pharamceutically acceptable carrier.

9. A composition according to claim 8, wherein the compound is present in an amount of 25-200 mg.

10. A method for treating hypertension in a patient in need of such treatment comprising administering to said patient an effective amount of a compound of claim 1.

11. A 1α,7α-Dithio-substituted spirolactone of general Formula I

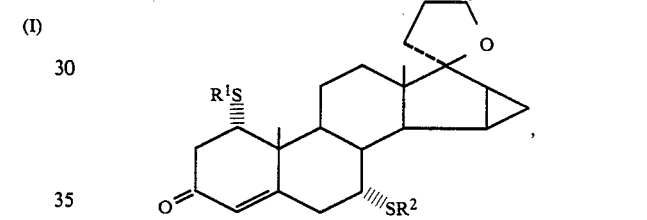

wherein
$R^1$ is $C_{1-3}$-alkyl and
$R^2$ is $C_{1-3}$-acyl.

12. A pharmaceutical composition useful for treating hypertension comprising an effective amount of a compound of claim 11 and a pharmaceutically acceptable carrier.

13. A composition according to claim 12, wherein the compound is present in an amount of 25-200 mg.

14. A method for treating hypertension in a patient in need of such treatment comprising administering to said patient an effective amount of a compound of claim 11.

* * * * *